(12) United States Patent
Yamamoto et al.

(10) Patent No.: US 7,787,116 B2
(45) Date of Patent: Aug. 31, 2010

(54) CUVETTE (75) Inventors: Norimasa Yamamoto, Kobe (JP);
Nobuhiro Kitagawa, Akashi (JP);
Takashi Yamato, Kakogawa (JP)

(73) Assignee: Sysmex Corporation, Kobe (JP)

( * ) Notice: Subject to any disclaimer, the term of this patent is extended or adjusted under 35 U.S.C. 154(b) by 0 days.

(21) Appl. No.: 12/020,375

(22) Filed: Jan. 25, 2008

(65) Prior Publication Data

US 2008/0123091 A1    May 29, 2008

Related U.S. Application Data (63) Continuation of application No. PCT/JP2006/312784, filed on Jun. 27, 2006.

(30) Foreign Application Priority Data

Jul. 27, 2005   (JP) ............... 2005-218097

(51) Int. Cl.
*G01N 21/01* (2006.01)
*G01N 1/10* (2006.01)
(52) U.S. Cl. ..................... 356/244; 356/246
(58) Field of Classification Search ............... 356/244, 356/246, 426–428, 432–440; 422/64–65, 422/102, 246
See application file for complete search history.

(56) References Cited

U.S. PATENT DOCUMENTS

| 3,977,794 | A | * | 8/1976 | Liedholz | 356/244 |
|---|---|---|---|---|---|
| 4,115,011 | A | * | 9/1978 | Brunsting | 356/246 |
| 4,229,104 | A | * | 10/1980 | Lahme et al. | 356/246 |
| 4,549,809 | A | * | 10/1985 | Minekane et al. | 356/436 |
| 4,560,269 | A | * | 12/1985 | Baldszun et al. | 356/246 |
| 4,634,576 | A | * | 1/1987 | Galle et al. | 422/102 |
| 5,284,624 | A | * | 2/1994 | Behnk | 422/102 |
| 5,582,796 | A | * | 12/1996 | Carey et al. | 422/65 |
| 5,587,129 | A | * | 12/1996 | Kurosaki et al. | 422/64 |
| 5,651,941 | A | * | 7/1997 | Stark et al. | 422/104 |
| 5,653,940 | A | * | 8/1997 | Carey et al. | 422/52 |
| 5,658,532 | A | * | 8/1997 | Kurosaki et al. | 422/64 |
| 2002/0009397 | A1 | * | 1/2002 | Hirono et al. | 422/104 |
| 2002/0155035 | A1 | * | 10/2002 | Kansy et al. | 422/102 |

(Continued)

FOREIGN PATENT DOCUMENTS

EP      661532 A2 *  7/1995

(Continued)

OTHER PUBLICATIONS

Opinion by the International Search Authority (PCT/ISA/237) mailed Sep. 26, 2006.

*Primary Examiner*—Sang Nguyen
(74) *Attorney, Agent, or Firm*—Brinks Hofer Gilson & Lione (57) ABSTRACT

A cuvette capable of suppressing the complication of the structure of each part of an analyzer and enabling the stirring of a specimen in a short time. The cuvette comprises: a first body part positioned on a bottom part side, having inner and outer surfaces of circular shape in horizontal cross section, and receiving a measuring beam; and a second body part positioned on an opening side, having an inner surface of non-circular shape in horizontal cross section and an outer surface of circular shape in horizontal cross section.

15 Claims, 9 Drawing Sheets

U.S. PATENT DOCUMENTS

2005/0282283 A1* 12/2005 Vozza-Brown et al. ...... 435/459

FOREIGN PATENT DOCUMENTS

| JP | 51-36177 | P | 3/1976 |
| JP | 57-144463 | P | 9/1982 |
| JP | 60-166843 | P | 8/1985 |
| JP | 61-202073 | U | 12/1986 |
| JP | 6-40848 | P | 5/1994 |
| JP | 7-43523 | U | 8/1995 |
| JP | 8-101209 | P | 4/1996 |
| JP | 8-299775 | P | 11/1996 |
| JP | 2002-196007 | P | 7/2002 |

* cited by examiner

CUVETTE

This application is a continuation of PCT/JP2006/312784, filed Jun. 27, 2006, which claims priority to Japanese Application No. JP2005-218097 filed Jul. 27, 2005. The entire contents of these applications are incorporated herein by reference.

BACKGROUND

1. Technical Field

The present invention relates to a cuvette, and more particularly, it relates to a cuvette employed for analysis of a specimen such as blood (including plasma or serum) or urine.

2. Background Information

Figure 16:
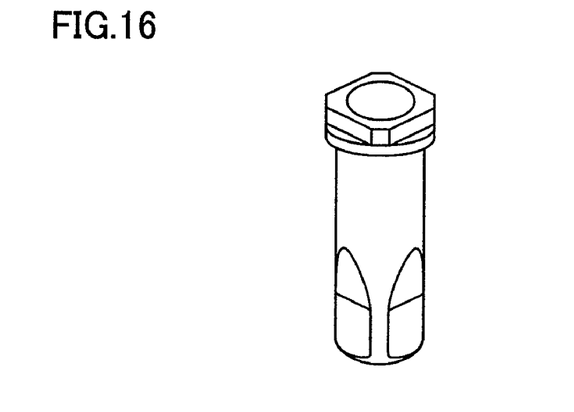
FIG. 16 is a perspective view showing a conventional cuvette.
Figure 17:
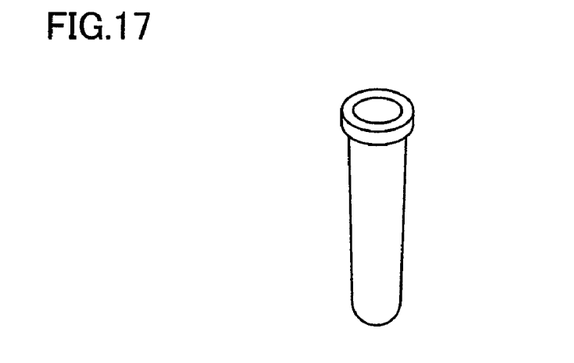
FIG. 17 is a perspective view showing a conventional cuvette.

Various shaped cuvettes are known in general. For example, Japanese Patent Laying-Open No. 8-101209 discloses a cuvette having a square cylindrical lower portion and a cylindrical upper portion and configured such that outer and inner surfaces of the lower portion each has a multangular shape in horizontal cross section, as shown in FIG. 16. Japanese Patent Laying-Open No. 2002-196007 discloses a cuvette configured such that outer and inner surfaces from an upper portion to a lower portion each has a circular shape in horizontal cross section, as shown in FIG. 17.

Figure 18:
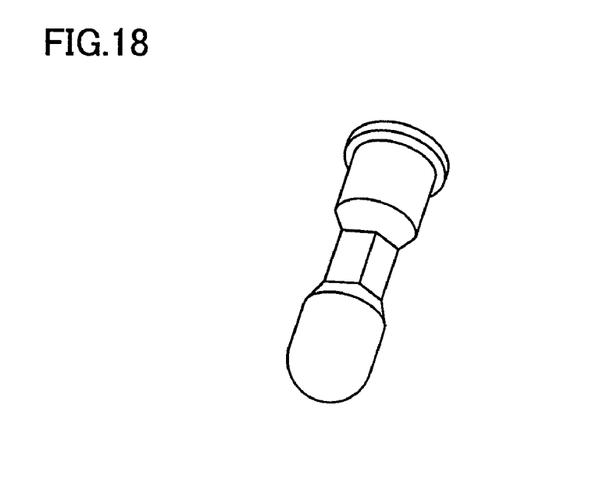
FIG. 18 is a perspective view showing a conventional cuvette.

Japanese Utility Model Laying-Open No. 6-40848 discloses a cuvette in which a central portion is formed in a square cylindrical shape, upper and lower portions arranged so as to hold the central portion therebetween are each formed in a cylindrical shape, and each of outer and inner surfaces of the central portion is configured to have a square shape in horizontal cross section, as shown in FIG. 18.

Each of the aforementioned cuvettes is employed for analysis of a specimen including steps of dispensing, stirring, and optically measuring the specimen and a reagent by automatically transferring the same on an analyzer. For example, each of the aforementioned cuvettes is transferred by grasping the upper portion of the cuvette with a transfer apparatus having a hand member capable of grasping the upper portion of the cuvette. A sample stored in the cuvette is stirred by vibrating the cuvette through drive of a vibration motor in a state of grasping the cuvette by the transfer apparatus. In the optical measurement, the cuvette storing the sample is irradiated with a measuring beam in a state where the cuvette is received in a receiving hole.

However, the cuvette in Japanese Patent Laying-Open No. 8-101209 shown in FIG. 16 is configured such that a measuring beam is applied to a square cylindrical portion of the lower portion of the cuvette. In such a structure, even when the cuvette inserted into a receiving hole is placed at a prescribed position, if the cuvette rotates at the position, an angle at which light enters from a light source is not constant with respect to a wall surface of the square cylindrical portion. In this case, the state of refraction or reflection of light by the wall surface varies, whereby there is a possibility that reproducibility of measurement results is deteriorated. Therefore, the analyzer must be configured such that the cuvette placed in the receiving hole does not rotate. Even in a case where the analyzer must be configured such that the cuvette placed in the receiving hole does not rotate, the analyzer must be configured such that a specific wall surface of the square cylindrical portion of the cuvette is placed so as to face the light source at least when the cuvette is inserted into the receiving hole. Therefore, in the cuvette disclosed in Japanese Patent Laying-Open No. 8-101209, structures of respective components of the analyzer including a transfer apparatus is disadvantageously complicated.

The cuvette in Japanese Utility Model Laying-Open No. 6-40848 shown in FIG. 18 is configured such that a measuring beam is applied to the square cylindrical portion of the central portion of the cuvette. Thus, this cuvette has a problem similar to that of the cuvette shown in FIG. 16.

In the cuvette in Japanese Patent Laying-Open No. 2002-196007 shown in FIG. 17, the inner surface of the cuvette has a circular shape in horizontal cross section, and hence a sample in the cuvette smoothly flows keeping a state where the sample is not sufficiently immingled, without disturbing the flow, even when vibration is applied to the cuvette. Thus, when vibration is applied to the cuvette to stir a specimen or a reagent in the cuvette, if stirring time is short, stirring may be insufficient depending on a condition such as ratio or viscosity of the specimen or the reagent. Consequently, in the cuvette disclosed in Japanese Patent Laying-Open No. 2002-196007, stirring of the sample disadvantageously requires long time.

SUMMARY OF THE INVENTION

The present invention has been proposed in order to solve the aforementioned problem, and an object of the present invention is to provide a cuvette capable of stirring a sample in a short time while suppressing respective components of an analyzer from complication.

A cuvette according to a first aspect of the present invention, which is a cuvette for containing a measurement sample therein, irradiated with a measuring beam for measuring characteristics of the measurement sample from a side part in an upright state when the cuvette is used, and having an opening, comprises a first body part located on a side of a bottom part, having inner and outer surfaces each formed in a circular shape in horizontal cross section, and irradiated with the measuring beam; and a second body part located on a side of the opening, having an inner surface formed in a non-circular shape in horizontal cross section and an outer surface formed in a circular shape in horizontal cross section.

A cuvette according to a second aspect of the present invention, which is a cuvette for containing a measurement sample therein, irradiated with a measuring beam for measuring characteristics of the measurement sample from a side part in an upright state when the cuvette is used, and having an opening, comprises: a first body part located on a side of a bottom part, having inner and outer surfaces each formed in a circular shape in horizontal cross section, and irradiated with the measuring beam; a second body part located on a side of the opening, having an inner surface formed in a non-circular shape in horizontal cross section; and a third body part located between the first body part and the second body part, and having an inner surface connecting the inner surface of the first body part and the inner surface of the second body part in a tapered manner.

DETAILED DESCRIPTION OF THE PREFERRED EMBODIMENTS

An embodiment of the present invention is hereinafter described with reference to the drawings.

The structure of a cuvette 1 according to an embodiment of the present invention is now described with reference to FIGS. 1 to 5.

The cuvette 1 according to the embodiment of the present invention is employed for storing a sample such as a specimen or a reagent when analyzing the specimen such as blood (including plasma or serum) or urine.

Figure 1:
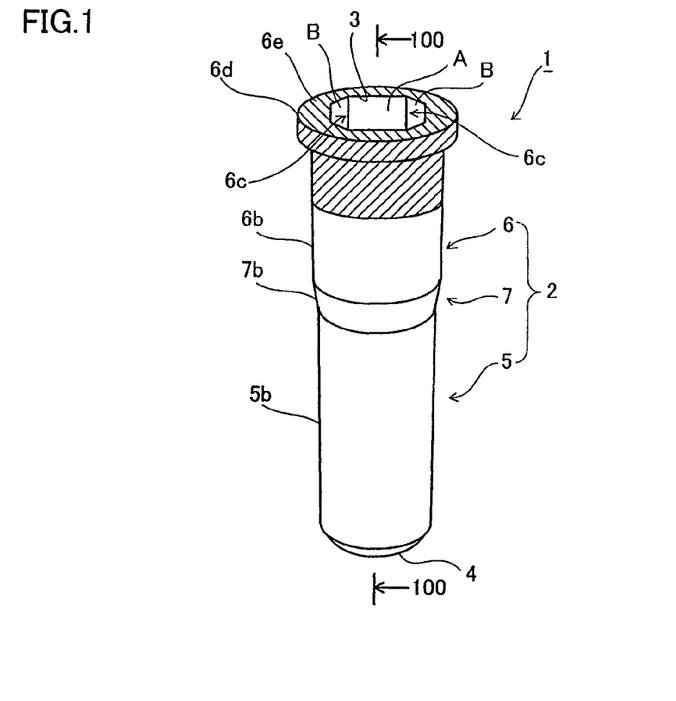
FIG. 1 is a perspective view showing a cuvette according to an embodiment of the present invention.
Figure 2:
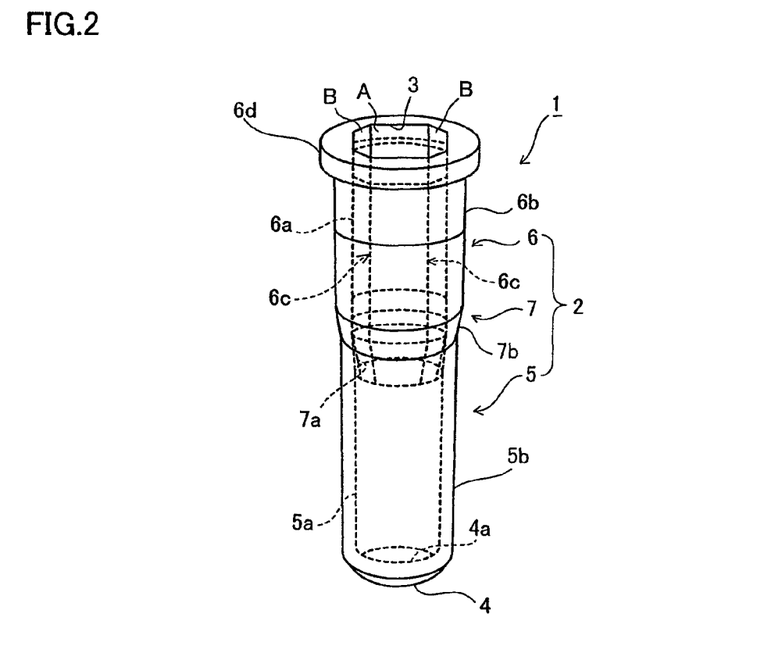
FIG. 2 is a perspective view showing the cuvette according to the embodiment of the present invention.
Figure 3:
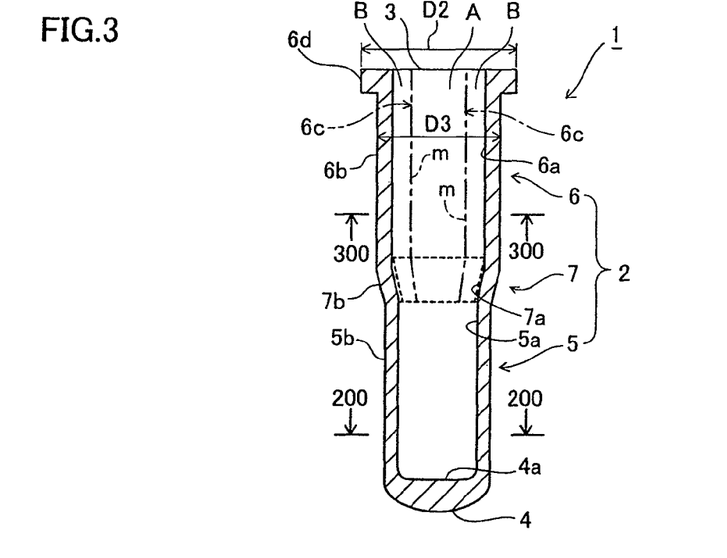
FIG. 3 is a vertical sectional view taken along the line 100-100 of the cuvette shown in FIG. 1.

The cuvette 1 according to this embodiment is formed by resin molding, employing clear and colorless polystyrene, as shown in FIGS. 1 to 3. This cuvette 1 includes a body part 2, an opening 3 provided on an upper end of the body part 2 and a bottom part 4 provided on a lower end of the body part 2. A sample such as a specimen or a reagent is dispensed into the cuvette 1 through the opening 3. As shown in FIG. 3, an upper surface 4a (inner bottom surface of the cuvette 1) of the bottom part 4 is formed in a flat surface shape as shown in FIG. 3. This upper surface 4a of the bottom part 4 is a horizontal surface in a state where the cuvette 1 is upright.

Figure 4:
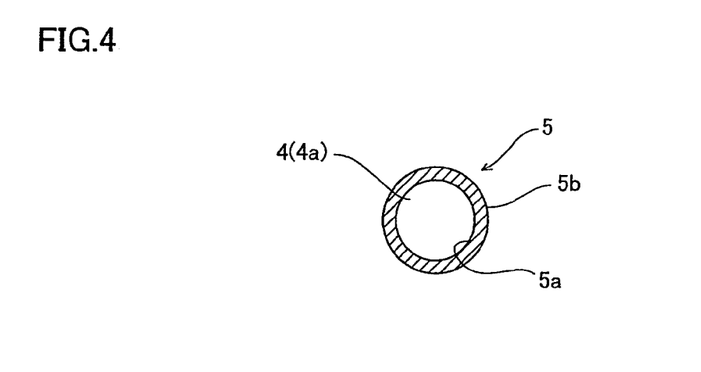
FIG. 4 is a horizontal sectional view taken along the line 200-200 of the cuvette shown in FIG. 3.

As shown in FIGS. 1 to 3, the body part 2 includes a first body part 5 located on a side of the bottom part 4, a second body part 6 located on a side of the opening 3 and a third body part 7 located between the first body part 5 and the second body part 6. The first body part 5 is a portion irradiated with a measuring beam in a detection part 28 of a specimen analyzer 20 described later and has translucency. As shown in FIG. 4, inner and outer surfaces 5a and 5b of the first body part 5 are each formed in a circular shape in horizontal cross section.

Figure 5:
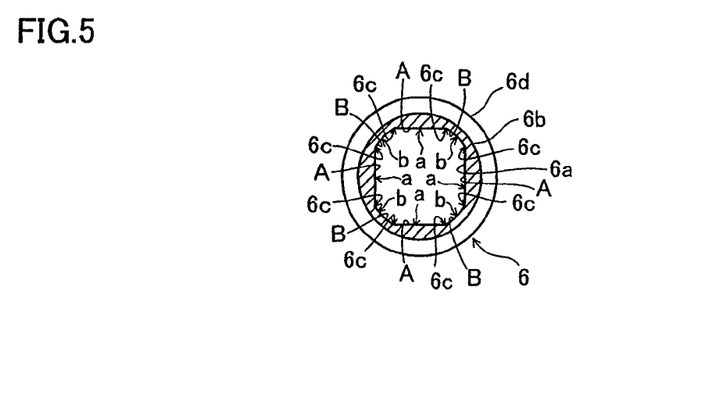
FIG. 5 is a horizontal sectional view taken along the line 300-300 of the cuvette shown in FIG. 3.

As shown in FIG. 5, an inner surface 6a of the second body part 6 is formed in a square shape with corners chamfered in horizontal cross section, an outer surface 6b of the second body part 6 is formed in a circular shape in horizontal cross section. More specifically, the inner surface 6a of the second body part 6 is formed by four principal straight lines a and four curved lines b shorter than the principal straight lines a in horizontal cross section. In other words, eight bent parts 6c are formed on bonding portions alternately bonding four principal flat surfaces A (see FIGS. 1 to 3) corresponding to the four principal sides a and four curved surfaces B (see FIGS. 1 to 3) corresponding to the four curved lines b on the inner surface 6a of the second body part 6. Sides m produced by bonding the flat surfaces A and the curved surfaces B on the bent parts 6c are shown by alternate long and short dash lines in FIG. 3. The sides m continue up to the third body part 7.

The area of a circle constituting the inner surface 5a of the first body part 5 is smaller than the area of a region surrounded by the inner surface 6a of the second body part 6 (region surrounded by the four straight lines a and the four curved lines b) in horizontal cross section. The circle constituting the inner surface 5a of the first body part 5 has a size larger than that of a circle inscribed in the inner surface 6a of the second body part 6 formed by the four straight lines a and the four curved lines b in horizontal cross section.

As shown in FIG. 1, a flange 6d grasped with a hand portion 23f or 27a when transferring the cuvette 1 in the specimen analyzer 20 described later is provided on an outer periphery of the upper end of the second body part 6. The outer surface of the flange 6d is formed in a circular shape in horizontal cross section.

The flange 6d of the outer surface 6b of the second body part 6 and a portion in the vicinity of the flange 6d (shaded (hatched) portion in FIG. 1) are coated with opaque black paint. The portions coated with the black paint are hereinafter referred to as "light absorption part 6e". The light absorption part 6e is a portion projecting to the outside from a measurement receiving hole 28c when the cuvette 1 is inserted into the measurement receiving hole 28c in the detection part 28 of the specimen analyzer 20 described later.

As shown in FIG. 2, an inner surface 7a of the third body part 7 is formed continuous with the four principal flat surfaces A and the four curved surfaces B constituting the inner surface 6a of the second body part 6. The inner surface 7a of the third body part 7 is tapered such that opposed surfaces are inclined symmetrical with respect to a central axis of the cuvette 1. The inner surface 7a of the third body part 7 connects the inner surface 6a of the second body part 6 and the inner surface 5a of the first body part 5 due to such a shape. Thus, the inner surface 7a of the third body part 7 is formed in a shape similar to the inner surface 6a of the second body part 6 in the vicinity of the second body part 6 and gradually comes close to the shape of the inner surface 5a of the first body part 5 (circular shape) as getting close to the first body part 5, in horizontal cross section. An outer surface 7b of the third body part 7 is formed in a circular shape in horizontal cross section and connects the outer surface 6b of the second body part 6 and the outer surface 5b of the first body part 5 in a tapered manner.

The structure of the specimen analyzer 20 employing the cuvette 1 is described with reference to FIGS. 3 and 6 to 11.

This specimen analyzer 20 has a function of analyzing a sample stored in the cuvette 1. The specimen analyzer 20 is constituted by a detection mechanism part 21 and a transport mechanism part 22 arranged on a front side of the detection mechanism part 21 as shown in FIGS. 6 and 7.

The detection mechanism part 21 has a function of optically measuring a measurement sample prepared by adding a reagent to a specimen. The detection mechanism part 21 includes a cuvette supply part 23, a rotary transport part 24, a specimen dispensing arm 25, two reagent dispensing arms 26, a cuvette transfer part 27 and a detection part 28.

Figure 7:
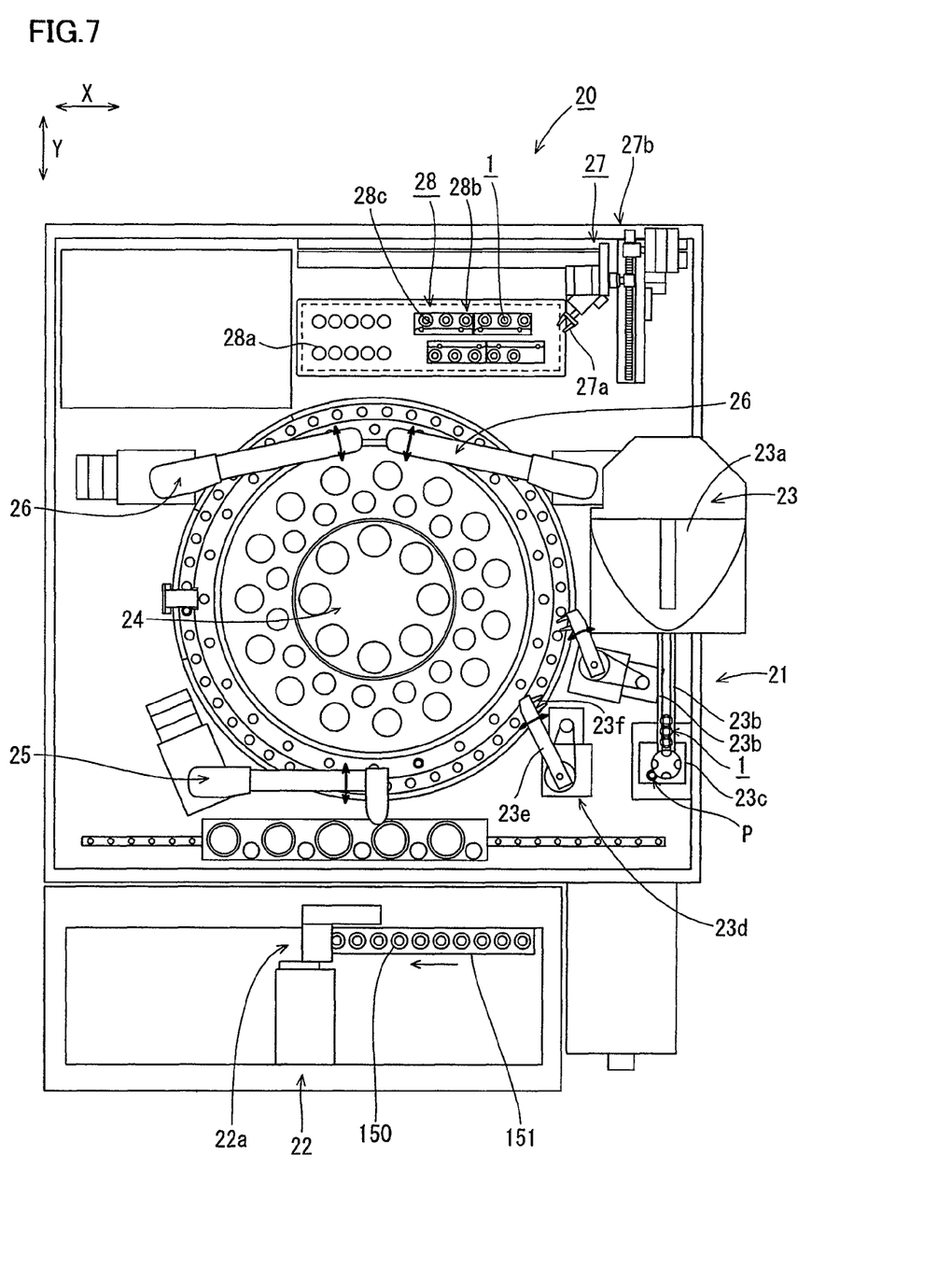
FIG. 7 is a plan view showing the overall structure of the specimen analyzer employing the cuvette according to the embodiment of the present invention.

As shown in FIG. 7, the transport mechanism part 22 has a function of transporting a rack 151 carrying a plurality of test tubes 150 storing specimens such as plasma, serum and urine to a suctional/dispensing position 22a.

Figure 6:
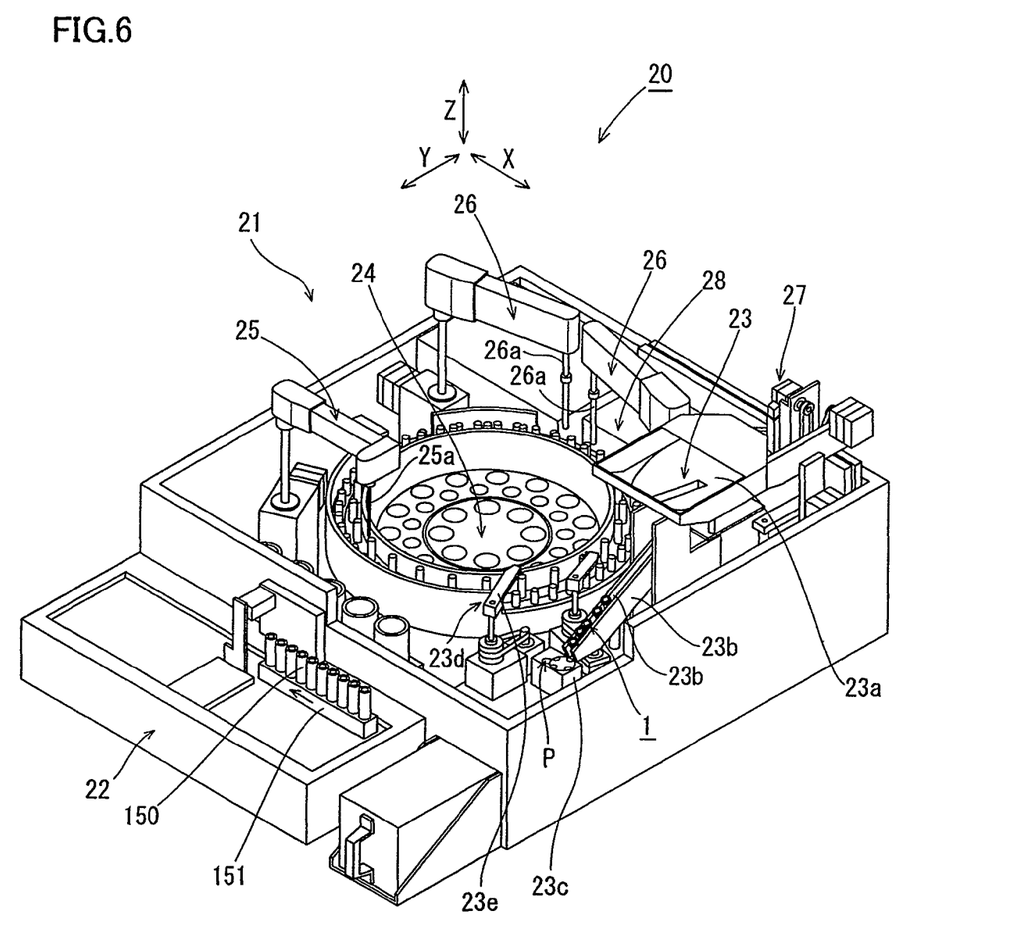
FIG. 6 is a perspective view showing the overall structure of a specimen analyzer employing the cuvette according to the embodiment of the present invention.

As shown in FIGS. 6 and 7, the cuvette supply part 23 has a hopper 23a capable of storing a plurality of the cuvettes 1, two induction plates 23b having slopes for sliding down the cuvettes 1 from the hopper 23a, a rotatable fulcrum 23c receiving the cuvettes 1 sliding down through the induction plates 23b and feeding the same to a pickup position P one by one, a supply catcher part 23d grasping the cuvettes 1 fed to the pickup position P with the fulcrum 23c one by one and successively supplying the same to the rotary transport part 24.

The interval D1 (see FIG. 8) of the induction plates 23b is smaller than the outer diameter D2 (see FIG. 3) of the flange 6d and larger than the diameter D3 (see FIG. 3) of the outer surface 6b of the second body part 6. Thus, the cuvette 1 is so formed as to slide down on the induction plates by putting the flange 6d on the two induction plates 23b.

Figure 9:
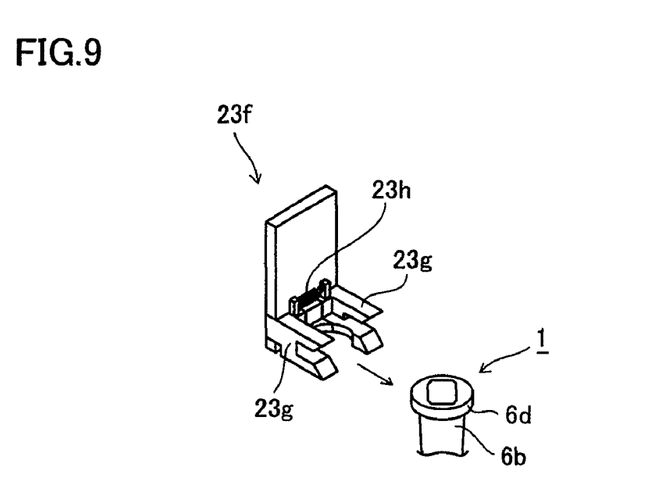
FIG. 9 is a perspective view showing a hand member of the specimen analyzer employing the cuvette according to the embodiment of the present invention and the cuvette.

As shown in FIGS. 6 and 7, the supply catcher part 23d is capable of holding and grasping the cuvette 1 with the hand member 23f (see FIG. 7) provided on a forward end of an arm part 23e. The supply catcher part 23d is configured such that the grasped cuvette 1 is supplied to the rotary transport part 24 by rotating the arm part 23e in a state of grasping the cuvette 1. As shown in FIG. 9, the hand member 23f has a pair of clip members 23g having a two-forked shape for clipping the flange 6d of the cuvette 1 from a horizontal direction, and a helical compression spring 23h urging the pair of clip members 23g in a direction in which the clip members 23g come close to each other. The flange 6d of the cuvette 1 is grasped with the hand member 23f by clipping with the two-forked shaped portion of the clip members 23g urged in the direction in which the clip members 22g come close to each other. The inside of the clip members 23g has a curved shaped corresponding to the circular outer surface 6b of the second body part 6 of the cuvette 1. Thus, the hand member 23f is capable of horizontally approaching the cuvette 1 regardless of the direction of the cuvette 1 and holding and grasping the cuvette 1.

As shown in FIGS. 6 and 7, the rotary transport part 24 is capable of placing a plurality of the cuvettes 1 and reagent containers (not shown) thereon. This rotary transport part 24 has a function of transporting the cuvettes 1 supplied from the cuvette supply part 23 and the reagent containers (not shown) storing reagents to be added to the specimen in the cuvettes 1 in a rotational direction.

The specimen dispensing arm 25 is configured such that the specimens in the test tubes 150 transported to the suctional/dispensing position 22a with the transport mechanism part 22 are sucked with a pipette part 25a (see FIG. 6) and prescribed quantities of the sucked specimens are dispensed into the cuvettes 1 placed on the rotary transport part 24 of the detection mechanism part 21.

The reagent dispensing arms 26 each has a function of sucking the reagents from the reagent containers (not shown) with the pipette part 26a (see FIG. 6) and dispensing the sucked reagents into the cuvettes 1 storing the specimens.

Figure 10:
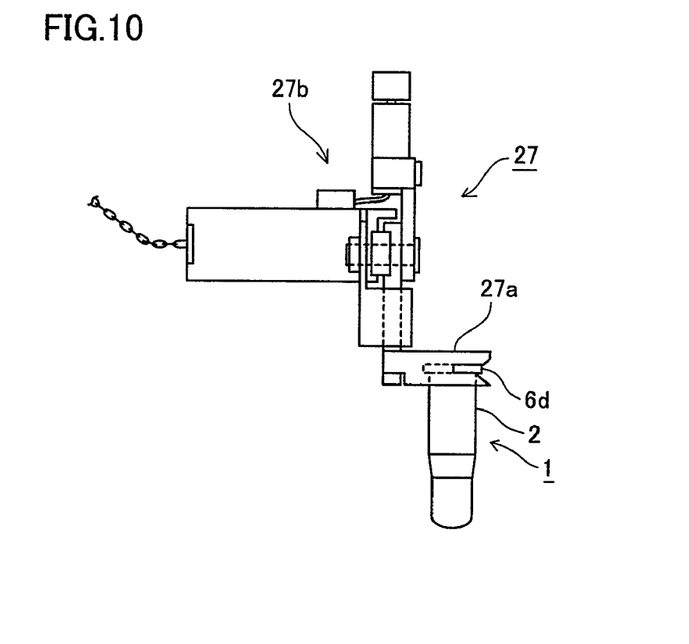
FIG. 10 is a side elevational view showing a cuvette transfer part of the specimen analyzer employing the cuvette according to the embodiment of the present invention and the cuvette.

The cuvette transfer part 27 has a function of transferring the cuvettes 1 between the rotary transport part 24 and the detection part 28. As shown in FIGS. 7 and 10, the cuvette transfer part 27 includes the hand member 27a for holding and grasping the cuvette 1 and a driving mechanism part 27b for moving and vibrating the hand member 27a. The cuvette transfer part 27 has a function of stirring the specimen and the reagent stored in the cuvette 1 by vibrating the hand member 27a with the driving mechanism part 27b in a state of grasping the cuvette 1. The structure of the hand member 27a is similar to that of the hand member 23f shown in FIG. 9.

The detection part 28 has a function of warming the specimens up to about 37° C. and a function of optically measuring the measurement samples prepared by mixing the specimens and the reagents. As shown in FIG. 7, the detection part 28 has warming receiving holes 28a receiving the cuvettes 1 in warming the cuvettes 1 and measurement parts 28b performing optical measurement.

Figure 11:
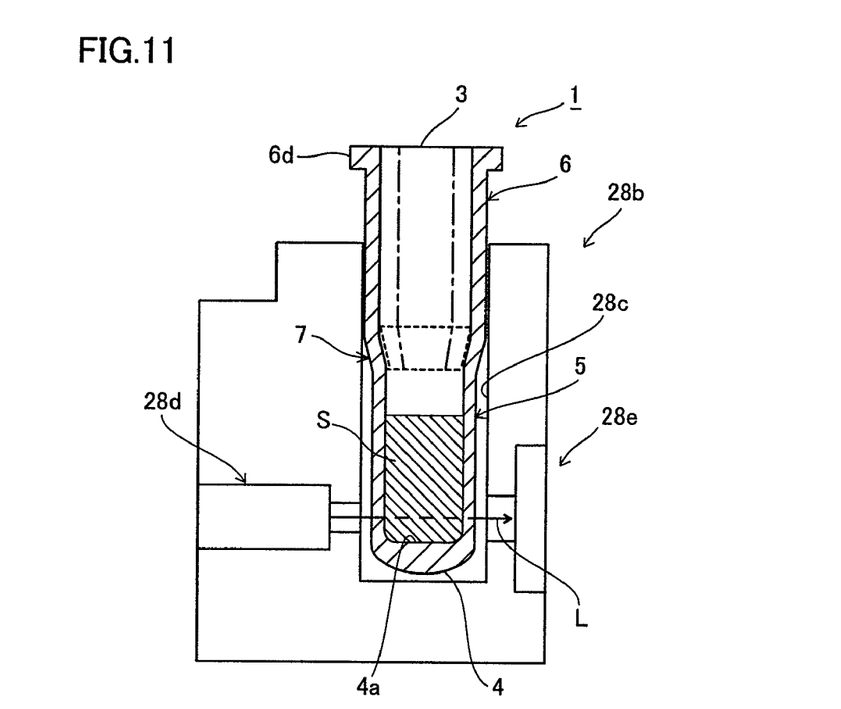
FIG. 11 is a sectional view showing a measurement part of the specimen analyzer employing the cuvette according to the embodiment of the present invention and the cuvette.

As shown in FIG. 11, the measurement parts 28b have the measurement receiving holes 28c receiving the cuvettes 1 storing the measurement samples, light source parts 28d provided at positions corresponding to the first body parts 5 in a state of inserting the cuvettes 1 into the measurement receiving holes 28c, and photoreceptive parts 28e provided at positions opposed to the light source parts 28d through the first body parts 5. The measurement receiving holes 28c each has a circular shape in horizontal cross section. The light source parts 28d each has a function of applying a measuring beam L having a prescribed wavelength to the first body part 5 of the cuvette 1 inserted into the measurement receiving hole 28c. The photoreceptive parts 28e each has a function of detecting transmitted light obtained by transmitting the measuring beam L applied by the light source part 28d through a measurement sample S.

A method of using the cuvette 1 in the specimen analyzer 20 is now described with reference to FIGS. 1, 6 to 8 and 11.

Figure 8:
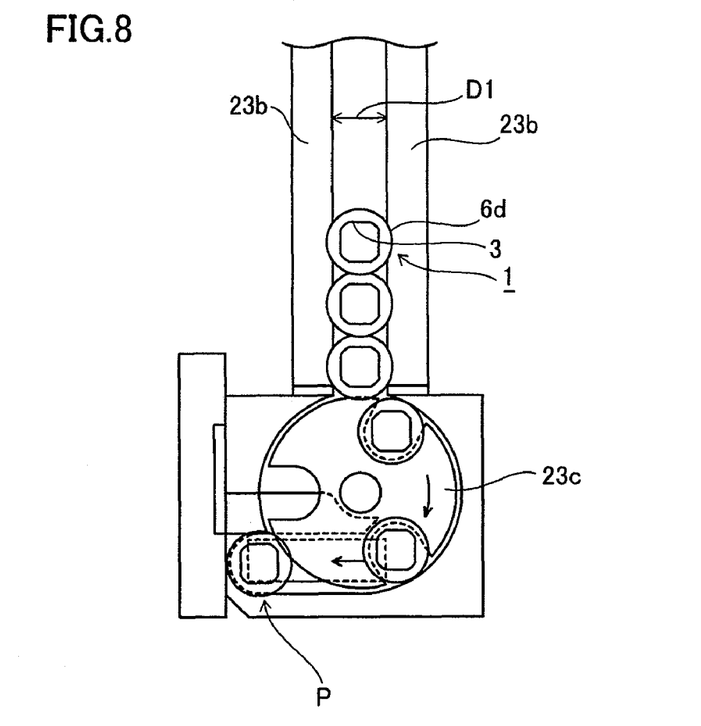
FIG. 8 is a plan view showing induction plates of the specimen analyzer employing the cuvette according to the embodiment of the present invention and the cuvettes.

As shown in FIGS. 6 and 7, the cuvette 1 supplied in the hopper 23a moves toward the fulcrum 23c while sliding down on the two induction plates 23b. At this time, the cuvette 1 has the flange 6d on its upper end as shown in FIG. 1 and hence the cuvette 1 slides down in a state where the flange 6d engages with upper surfaces of the two induction plates 23b as shown in FIG. 8. The cuvette 1 reaching the fulcrum 23c is transported to the pickup position P with the fulcrum 23c. The cuvette 1 at the pickup position P is supplied to the rotary transport part 24 grasped with the supply catcher part 23d.

The specimen dispensing arm 25 first dispenses a prescribed quantity of the specimen in the test tube 150 of the transport mechanism part 22 into the cuvette 1 supplied to the rotary transport part 24. The cuvette transfer part 27 carries the cuvette 1 dispensed with the specimen thereinto to the detection part 28 after the rotary transport part 24 transports the same to a prescribed position. The cuvette transfer part 27 takes out the cuvette 1 from the warming receiving hole 28a after the cuvette 1 is inserted into the warming receiving hole 28a having a warming function and warmed for a prescribed time. The reagent dispensing arm 26 adds the reagent to the specimen in the cuvette 1.

After the specimen and the reagent are added in the cuvette 1, the driving mechanism part 27b of the cuvette transfer part 27 vibrates the hand portion 27a so that the specimen and the reagent in the cuvette 1 are stirred. An operation of stirring the specimen and the reagent by the cuvette transfer part 27 is hereinafter described in detail.

When the reagent is dispensed into the cuvette 1, the specimen and the reagent are accumulated in the first body part 5 positioned on the side of the bottom part 4 due to its own weight. The driving mechanism part 27b vibrates the hand member 27a in a state where the hand member 27a grasps the cuvette 1 storing the specimen and the reagent. This vibration generates a horizontal rotational flow along the inner surface 5a of the first body part 5 in the sample in the cuvette 1. The sample rotationally flowing moves toward the inner surface 5a of the first body part 5 with centrifugal force. The sample having collided with the inner surface 5a of the first body part 5 moves upward along the inner surface 5a of the first body part 5. The sample having moved upward while rotating as described above reaches the second body part 6 through the third body part 7 and rotates along the inner surface 6a of the second body part 6.

According to this embodiment, the bent parts 6c is provided on the inner surface 6a of the second body part 6, whereby the flow of the sample along the inner surface 6a of the second body part 6 is disturbed by the bent parts 6c. The sample, the flow of which is disturbed by the bent parts 6c, flows down to the first body part 5 due to its own weight. Thus, the specimen and the reagent are stirred to prepare the measurement sample.

The cuvette 1 storing the measurement sample is transferred to the detection part 28 with the cuvette transfer part 27 again and inserted into the measurement receiving hole 28c of the part 28b. As shown in FIG. 11, the measurement sample S of the first body part 5 is irradiated with the measuring beam L from the light source part 28d and the photoreceptive part 28e detects the transmitted light. The data of this transmitted light is analyzed, thereby analyzing the specimen. The flange 6d projects upward from the measurement receiving hole 28c so that the cuvette 1 inserted into the measurement receiving hole 28c is taken out by grasping the same with the aforementioned hand member 27a. The portion (light absorption part 6e) of the cuvette 1 projecting from the measurement receiving hole 28c is coated with the black paint, whereby the light absorption part 6e absorbs light from the outside. Thus, the light from the outside entering the upper portion of the cuvette 1 projecting from the measurement receiving hole 28c is inhibited from entering the photoreceptive part 28e through the cuvette 1 and the measurement sample stored in the cuvette 1.

In some measurement items, optical measurement is performed while stirring the measurement sample. In such cases, a magnetic agitator (not shown) is put into the cuvette 1, and measurement is performed while stirring the sample in the cuvette 1 by rotating the magnetic agitator with magnetic force from the outside.

According to this embodiment, as hereinabove described, the bent parts 6c is provided on the inner surface 6a of the second body part 6 located on the side of the opening 3, whereby the bent parts 6c disturbs the flow of the specimen and the reagent at the time of stirring the specimen and the reagent by the cuvette transfer part 27. Thus, stirring of the specimen and the reagent can be facilitated and hence time required for stirring the sample can be reduced. The outer surface 6b of the second body part 6 is formed in the circular shape in horizontal cross section, whereby resin molding can easily be performed as compared with a case where the outer surface 6b of the second body part 6 is formed in a non-circular shape in horizontal cross section.

According to this embodiment, as hereinabove described, each of the inner and outer surfaces 5a and 5b of the first body part 5 irradiated with the measuring beam is formed in the circular shape in horizontal cross section. Therefore, there does not occur a problem that the angle of the light entering from the light source with respect to a wall surface of the square cylindrical portion is not constant depending on a direction which the cuvette faces as in a cuvette shown in FIG. 16, even when the cuvette 1 is inserted into the measurement receiving hole 28c in any direction. Therefore, results of the measurement can be stabilized irrespective of the direction which the cuvette 1 faces, and hence a mechanism for inserting the cuvette 1 while a specific surface of the cuvette 1 faces the light source part 28d when the cuvette 1 is inserted into the measurement receiving hole 28c of the detection part 28 can be omitted. Thus, the structure of the specimen analyzer 20 can be suppressed from complication.

According to this embodiment, as hereinabove described, the measuring beam is applied to the first body part 5 located on the side of the bottom part 4, whereby the necessary quantity of the sample to be stored in the cuvette 1 for applying the measuring beam to the sample can be reduced. Thus, the measurement can be performed for a small quantity of the sample.

According to this embodiment, as hereinabove described, the inner surface 6a of the second body part 6 is formed in the square shape with the chamfered corners in horizontal cross section, whereby the eight bent parts 6c can be provided. Such a shape is a relatively simple shape, and hence resin molding can easily be performed. The corners of the square are chamfered, whereby the shape constituted by the inner surface 6a of the second body part 6 can be close to the circular shape of the outer surface 6b of the second body part 6. Thus, the area of the region surrounded by the inner surface 6a of the second body part 6 can be increased and hence the volume in the cuvette 1 can sufficiently be ensured while improving stirring function.

According to this embodiment, as hereinabove described, the inner surface 7a of the third body part 7 is so inclined as to broaden upward and narrow downward, whereby the sample stored in the first body part 5 can easily be moved to the upper second body part 6 along the inner surface 7a of the third body part 7 at the time of stirring. The sample reaching the second body part 6 at the time of stirring can be smoothly flown down to the first body part 5 without staying in the second body part 6 after completing stirring.

According to this embodiment, as hereinabove described, the area of the region surrounded by the inner surface 5a of the first body part 5 is smaller than the area of the region surrounded by the inner surface 6a of the second body part 6 in horizontal cross section. Thus, the height of the sample required for optical measurement can be ensured by a small quantity of the sample. The area of the region surrounded by the inner surface 6a of the second body part 6 is larger than the area of the region surrounded by the inner surface 5a of the first body part 5 in horizontal cross section. Therefore, the pipette part 25a of the specimen dispensing arm 25 or the pipette part 26a of the reagent dispensing arm 26 can easily be inserted into the cuvette 1.

According to this embodiment, as hereinabove described, the size of the circle constituting the inner surface 5a of the first body part 5 is identical with or smaller than the circle inscribed in the inner surface 6a of the second body part 6 in horizontal cross section. Therefore, centrifugal force applied to the sample in the first body part 5 is larger than centrifugal force applied to the sample in the second body part 6 when the sample is stirred. Thus, the flow of the sample in the second body part 6, to which the larger centrifugal force is applied, is disturbed by the bent parts 6c of the second body part 6, and hence stirring can further be facilitated.

According to this embodiment, as hereinabove described, the outer surface 6a of the second body part 6 is formed in a circular shape in horizontal cross section on the region in the vicinity of a lower side of the flange 6d. Thus, the cuvette 1 can smoothly slide down without getting stuck on the way, when the cuvette 1 slides down while engaging with the upper surface of the induction plates 23b. The outer surface 6b of the second body part 6 has the circular shape in horizontal cross section and hence can easily be clipped with the clip members 23g of the supply catcher part 23d irrespective of the direction which the cuvette 1 faces.

According to this embodiment, as hereinabove described, the light absorption part 6e is provided on the upper portion of the second body part 6, whereby the light absorption part 6e can absorb the light from the outside. Thus, the light from the outside can be inhibited from entering the photoreceptive parts 28e during measurement, and hence the light from the outside can be inhibited from influencing results of the measurement.

According to this embodiment, as hereinabove described, the upper surface 4a of the bottom part 4 of the cuvette 1 is formed in a flat surface shape. Thus, the magnetic agitator does not get stuck on the upper surface 4a of the bottom part 4 when the sample is stirred by rotating the magnetic agitator on the upper surface 4a of the bottom part 4, and hence the magnetic agitator can easily be rotated on the upper surface 4a of the bottom part 4 of the cuvette 1.

The embodiment disclosed this time must be considered as illustrative in all points and not restrictive. The range of the present invention is shown not by the above description of the embodiment but by the scope of claim for patent, and all modifications within the meaning and range equivalent to the scope of claim for patent are included.

Figure 12:
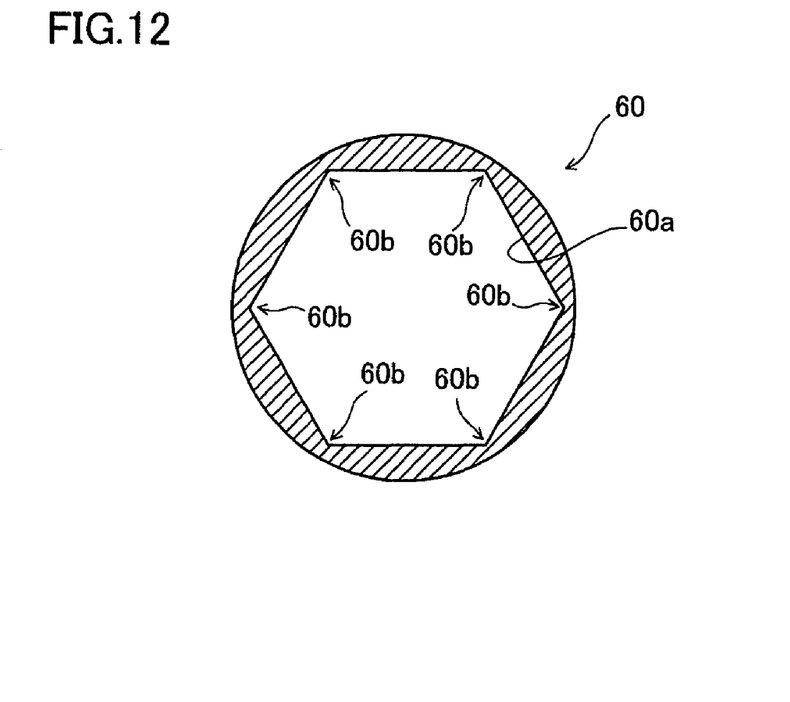
FIG. 12 is a horizontal sectional view of a second body part of a cuvette according to a first modification of the embodiment of the present invention.
Figure 13:
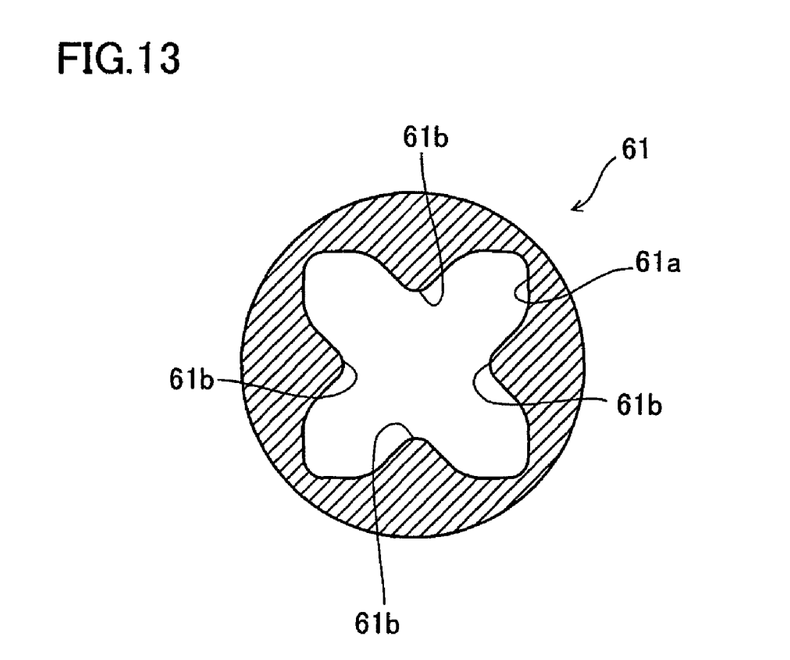
FIG. 13 is a horizontal sectional view of a second body part of a cuvette according to a second modification of the embodiment of the present invention.
Figure 14:
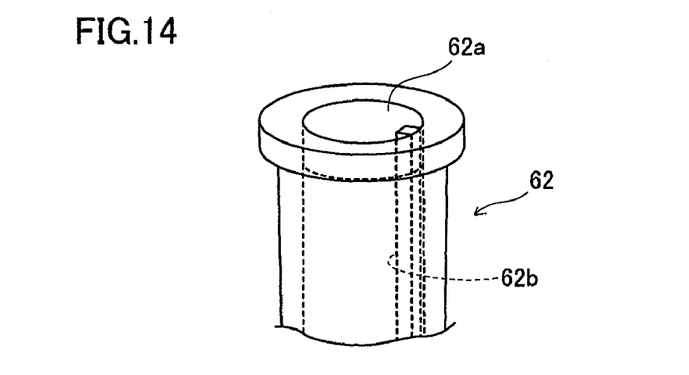
FIG. 14 is a perspective view showing an inner surface of a second body part of a cuvette according to a third modification of the embodiment of the present invention.

For example, while the inner surface 6a of the second body part 6 is formed in the square shape with the corners chamfered in horizontal cross section in the aforementioned embodiment, the present invention is not restricted to this but the inner surface 6a of the second body part 6 may alternatively be formed in the multangular shape other than the square shape in horizontal cross section. The inner surface 6a of the second body part 6 may alternatively be formed to have at least one projecting portion in horizontal cross section. For example, as in a second body part 60 of a cuvette according to a first modification shown in FIG. 12, an inner surface 60a of the second body part 60 may be formed in a hexagonal shape in horizontal cross section. Also in the second body part 60 of the cuvette according to this first modification, six bent parts 60b are formed on the inner surface 60a and stirring of a specimen and a reagent can be facilitated, and hence stirring can be preformed in a short time. As in a second body part 61 of a cuvette according to a second modification shown in FIG. 13, the inner surface 61a of the second body part 61 may be so formed as to be undulating (to have four projecting portions 61b) in horizontal cross section, or as in a second body part 62 of a cuvette according to a third modification shown in FIG. 14, a rib 62b (one projecting portion) projecting so as to linearly extend in a direction perpendicular to an inner surface 62a of the second body part 62 may be provided. Also in the second body part 61 or 62 of the cuvette according to the second or third modification, stirring of a specimen and a reagent can be facilitated and hence stirring of the sample can be performed in a short time. A needle-shaped, conical shaped, or cylindrical shaped projection (projecting portion) (not shown) may be provided on the inner surface of the second body part so that stirring of the sample in the cuvette can be facilitated.

While the inner surface 7a of the third body part 7 is tapered such that the opposed surfaces are inclined symmetrical with respect to the central axis of the cuvette 1 in the aforementioned embodiment, the present invention is not restricted to this. For example, the third body part may alternatively be formed such that only a part of the inner surface is inclined while the inner surface other than this part is not inclined, and also formed so as to connect the inner surfaces of the first body part and the second body part.

Figure 15:
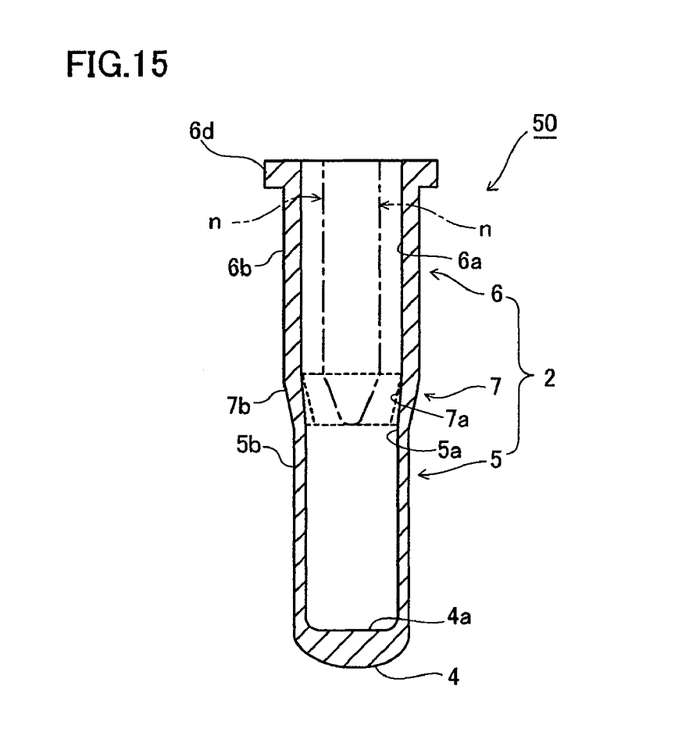
FIG. 15 is a vertical sectional view of a cuvette according to a fourth modification of the embodiment of the present invention.

While the two alternate long and short dash lines m gradually narrow toward a lower part in the third body part 7 as shown in FIG. 3 in the aforementioned embodiment, the present invention is not restricted to this but two alternate long and short dash lines n may alternatively rapidly narrow in a third body part 7 as in a cuvette 50 according to a fourth modification shown in FIG. 15. The two alternate long and short dash lines n shown in FIG. 15 and the two alternate long and short dash lines m shown in FIG. 3 are common in terms of narrowing toward the lower part in the third body part 7. However, the alternate long and short dash lines n according to the fourth modification shown in FIG. 15 rapidly narrow as compared with the alternate long and short dash lines m in FIG. 3 and substantially intersect with each other at a portion connecting the first body part 5 and the third body part 7. Also in the cuvette according to the fourth modification, the sample can easily be moved from the first body part 5 to the upper second body part 6 along the inner surface 7a of the third body part 7 at the time of stirring. The sample reaching the second body part 6 at the time of stirring can smoothly be flown down to the first body part 5 without staying in the second body part 6 after completing stirring.

While the light absorption part 6e is colored with a black color in the aforementioned embodiment, the present invention is not restricted to this but the light absorption part 6e may alternatively be coated with other color paint similar to black paint such as dark brown paint or deep indigo paint. These colors can also absorb lights having a large number of wavelengths. A specimen analyzer 20 may be provided with an optical filter on the photoreceptive part 28e of the detection part 28 so that only light having a specific wavelength is detected. In such a case, the color of the light absorption part 6e is not restricted to black or the color similar to black, but the color absorbing at least the light having the specific wavelength may be applicable.

While the outer side of the light absorption part 6e of the cuvette 1 is coated with the black paint in the aforementioned embodiment, the present invention is not restricted to this but the inner side of the cuvette 1 may alternatively be coated with the black paint.

While the light absorption part 6e is coated with the black paint in the aforementioned embodiment, the present invention is not restricted to this but the light absorption part may alternatively be formed by resin molding employing a material previously colored with black.

While the portion of the cuvette 1 other than the light absorption part 6e is clear and colorless in the aforementioned embodiment, the present invention is not restricted to this. For example, the portion other than the first body part 5, which is the portion other than light absorption part 6e may not be clear and colorless, so far as at least the first body part 5 has sufficiently translucency in order to perform optical measurement.

While the measurement sample prepared by adding the specimen to the reagent is employed in the aforementioned embodiment, the present invention is not restricted to this but a specimen with no reagent added thereto may be alternatively employed as the measurement sample.

The invention claimed is:

1. A cuvette having an opening and configured to contain a measurement sample therein, which is irradiated sideways by a measuring beam, while being in an upright position in use, to measure characteristics of the measurement sample, comprising:
   a first section to be irradiated by the measuring beam, the first section being located near a bottom of the cuvette and having inner and outer surfaces each being circular in horizontal cross section, and;
   a second section being located near the opening, the second section having inner and outer surfaces being non-circular and circular respectively in horizontal cross section.

2. The cuvette according to claim 1, wherein there is at least one angled corner formed in the inner surface of the second section.

3. The cuvette according to claim 2, wherein the inner surface of the second section is substantially polygonal in the horizontal cross section.

4. The cuvette according to claim 2, wherein the inner surface of the second section is polygonal with rounded corners in the horizontal cross section.

5. The cuvette according to claim 4, wherein the inner surface of the second section is substantially square in the horizontal cross section.

6. The cuvette according to claim 1, wherein the inner surface of the second section has at least one projection in the horizontal cross section.

7. The cuvette according to claim 1, wherein the second section comprises a flange provided near the opening.

8. The cuvette according to claim 7, wherein the outer surface of the second section is circular in the horizontal cross section in a region lower from the flange.

9. The cuvette according to claim 1, wherein the first section has a bottom inside thereof which is substantially flat.

10. The cuvette according to claim 1, wherein the second section comprises a light absorbing part for absorbing light.

11. The cuvette according to claim 10, wherein the light absorbing part is colored in black or similar color.

12. The cuvette according to claim 11, wherein the light absorbing part is coated in black or similar color.

13. The cuvette according to claim 1, further comprising
   a third section having a tapered inner surface connecting the inner surface of the first section and the inner surface of the second section,
   wherein the horizontal cross section defined by the inner surface of the second section is larger in area than the horizontal cross section defined by the inner surface of the first section, and
   wherein the inner surface of the third section is tapered so as to become wider as going upward and narrower as going downward.

14. The cuvette according to claim 13, wherein a horizontal circle defined by the inner surface of the first section is equal to or smaller than a horizontal circle inscribed in the inner surface of the second section.

15. A cuvette having an opening and configured to contain a measurement sample therein, which is irradiated sideways by a measuring beam, while being in an upright position in use, to measure characteristics of the measurement sample, comprising:
   a first section to be irradiated by the measuring beam, the first section is located near a bottom of the cuvette and having inner and outer surfaces each being circular in horizontal cross section;
   a second section being located near the opening, the second section having inner and outer surfaces being non-circular and circular respectively in horizontal cross section; and
   a third section being located between the first section and the second section and having an inner surface connecting the inner surface of the first section and the inner surface of the second section in a tapered manner.

* * * * *